United States Patent
Militello et al.

(10) Patent No.: US 12,365,902 B2
(45) Date of Patent: Jul. 22, 2025

(54) COMPOSITIONS AND METHODS OF GENERATING NOVEL amiRNA

(71) Applicant: Mirimus, Inc., Brooklyn, NY (US)

(72) Inventors: Giuseppe Militello, New York, NY (US); Christof Fellmann, Berkeley, CA (US); Johannes Zuber, Vienna (AT)

(73) Assignee: Mirimus, Inc., Brooklyn, NY (US)

( * ) Notice: Subject to any disclaimer, the term of this patent is extended or adjusted under 35 U.S.C. 154(b) by 0 days.

(21) Appl. No.: 18/899,181

(22) Filed: Sep. 27, 2024

(65) Prior Publication Data
US 2025/0027088 A1 Jan. 23, 2025

Related U.S. Application Data

(63) Continuation of application No. PCT/US2023/012483, filed on Feb. 7, 2023.

(60) Provisional application No. 63/325,207, filed on Mar. 30, 2022.

(51) Int. Cl.
*C12N 15/113* (2010.01)

(52) U.S. Cl.
CPC .... *C12N 15/1137* (2013.01); *C12N 2310/141* (2013.01); *C12N 2310/531* (2013.01); *C12Y 301/03067* (2013.01)

(58) Field of Classification Search
CPC ........ C12N 2310/141; C12N 2310/531; C12N 15/111; C12N 15/113; C12N 15/1137
See application file for complete search history.

(56) References Cited

U.S. PATENT DOCUMENTS

| | | |
|---|---|---|
| 11,957,114 B2 | 4/2024 | Premsrirut |
| 2011/0160286 A1 | 6/2011 | Xu |
| 2015/0018539 A1 | 1/2015 | Fellmann |
| 2018/0148723 A1 | 5/2018 | Ge et al. |
| 2018/0305689 A1 | 10/2018 | Saetrom et al. |
| 2021/0054405 A1 | 2/2021 | Kotin |

FOREIGN PATENT DOCUMENTS

| | | |
|---|---|---|
| WO | 2019108644 A1 | 6/2019 |
| WO | 2024097892 A1 | 5/2024 |

OTHER PUBLICATIONS

WIPO/ISA/US, International Search Report and Written Opinion issued in International Application No. PCT/US2023/012483 on May 23, 2023, 13 pages.
Jin, W., et al. "Structural basis for pri-miRNA recognition by Drosha." Molecular Cell 78.3 (2020): 423-433.
Lagos-Quintana, M., et al. "Identification of novel genes coding for small expressed RNAs." Science 294.5543 (2001): 853-858.
Lagos-Quintana, M., et al. "Identification of tissue-specific microRNAs from mouse." Current Biology 12.9 (2002): 735-739.
Lau, N. C., et al. "An abundant class of tiny RNAs with probable regulatory roles in Caenorhabditis elegans." Science 294.5543 (2001): 858-862.
Lee, R. C., et al. "An extensive class of small RNAs in Caenorhabditis elegans." Science 294.5543 (2001): 862-864.
Llave, C., et al. "Endogenous and silencing-associated small RNAs in plants." The Plant Cell 14.7 (2002): 1605-1619.
Mourelatos, Z., et al. "miRNPs: a novel class of ribonucleoproteins containing numerous microRNAs." Genes & Development 16.6 (2002): 720-728.
Park, W., et al. "Carpel Factory, a Dicer homolog, and HEN1, a novel protein, act in microRNA metabolism in *Arabidopsis thaliana*." Current Biology 12.17 (2002): 1484-1495.
Reinhart, B. J., et al. "MicroRNAs in plants." Genes & Development 16.13 (2002): 1616-1626.

*Primary Examiner* — J. E. Angell
(74) *Attorney, Agent, or Firm* — J. Peter Paredes; Amin Wasserman Gurnani LLP

(57) ABSTRACT

Provided herein are Compositions and Methods of Generating Novel amiRNA's. Provided herein are methods for producing or generating one or more amiRNAs; also provided are constructs and compositions useful in the methods. The methods and constructs provided in this disclosure are highly efficient methods for production of a new generation of amiRNAs.

9 Claims, 11 Drawing Sheets

Specification includes a Sequence Listing.

| | Guide 1 | Guide 2 | Guide 3 | Guide 4 | Guide 5 | Guide 6 | Guide 7 | Average |
|---|---|---|---|---|---|---|---|---|
| miR155 | 67.19% | 74.91% | 53.32% | 67.65% | 46.54% | 68.78% | 82.62% | 65.86% |
| miRE | 64.95% | 75.01% | 57.62% | 62.76% | 65.05% | 69.47% | 81.99% | 68.12% |
| Let7a3_Loop | 72.20% | 76.58% | 63.00% | 65.42% | 66.76% | 65.44% | 84.15% | 70.51% |
| miR26a1_Loop | 69.02% | 78.08% | 62.83% | 68.68% | 73.09% | 71.91% | 84.94% | 72.65% |
| Let7a2_Loop | 69.17% | 78.09% | 65.11% | 66.66% | 70.51% | 73.77% | 85.51% | 72.69% |
| miR26a1_WT | 70.71% | 80.25% | 69.63% | 72.24% | 70.23% | 77.27% | 85.94% | 75.18% |
| Let7a1_All | 69.02% | 78.01% | 72.40% | 71.63% | 71.67% | 78.16% | 86.20% | 75.30% |
| Let7a1_Loop | 71.06% | 78.45% | 72.77% | 69.91% | 71.83% | 78.25% | 86.49% | 75.54% |
| Let7a2_All | 72.07% | 79.74% | 71.80% | 72.78% | 73.08% | 74.54% | 87.48% | 75.93% |
| miR26a1_Stem | 70.43% | 80.93% | 69.09% | 73.96% | 73.37% | 78.35% | 85.67% | 75.97% |
| Let7c_All | 70.36% | 77.82% | 73.40% | 73.87% | 74.68% | 76.09% | 86.49% | 76.10% |
| miR26b_All | 70.38% | 80.72% | 73.49% | 75.29% | 75.69% | 70.98% | 88.12% | 76.38% |
| Let7f2_All | 73.02% | 78.51% | 75.10% | 72.33% | 72.65% | 79.36% | 87.43% | 76.91% |
| Let7f1_All | 74.04% | 79.91% | 73.57% | 73.29% | 73.80% | 78.23% | 87.39% | 77.18% |
| Let7a3_All | 74.69% | 78.24% | 77.19% | 75.71% | 73.47% | 78.91% | 89.09% | 78.18% |
| miR26a1_Base | 74.45% | 79.06% | 77.96% | 75.40% | 70.76% | 80.78% | 89.15% | 78.22% |
| miR26a1_All | 73.38% | 82.05% | 73.22% | 74.76% | 74.40% | 80.47% | 89.86% | 78.31% |
| miR26a2_Base | 73.79% | 82.85% | 77.72% | 77.55% | 79.57% | 82.49% | 87.97% | 80.28% |
| miR26a2_Stem | 76.38% | 80.92% | 79.46% | 77.38% | 78.03% | 81.02% | 90.28% | 80.50% |

FIG. 2B

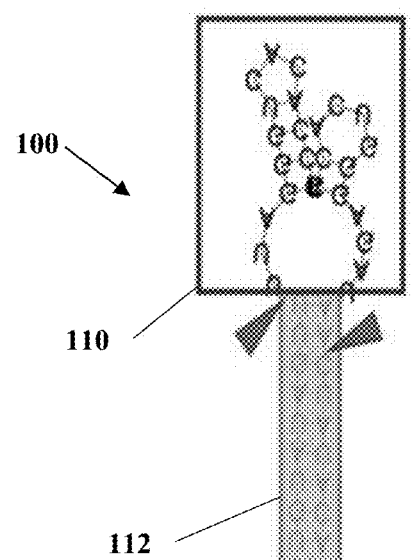
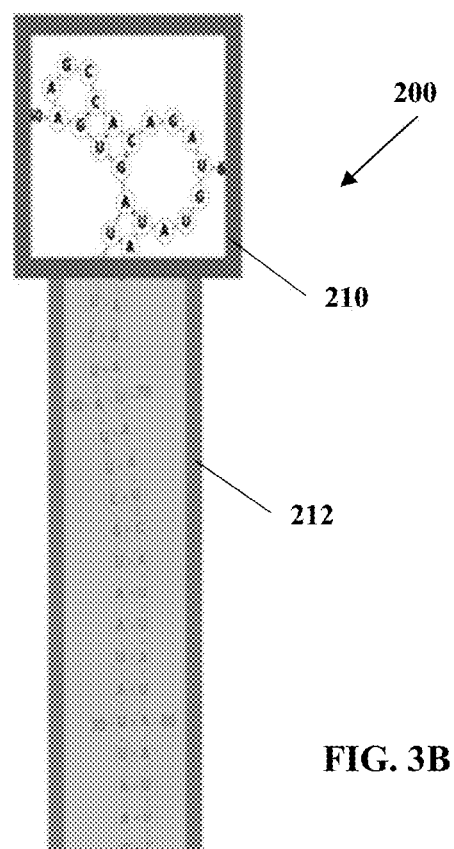
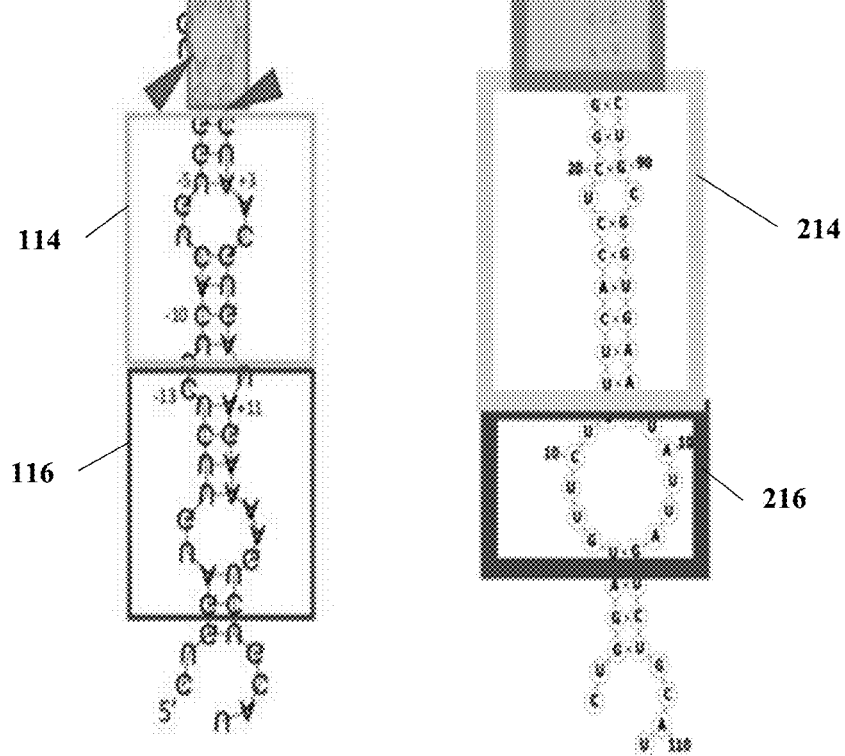
FIG. 3A
FIG. 3B

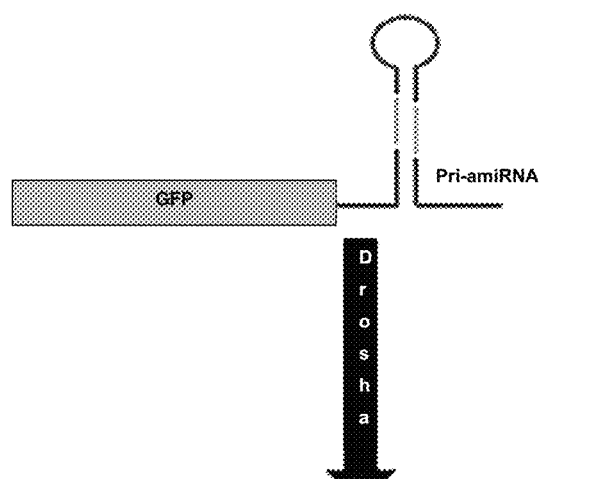
FIG. 7
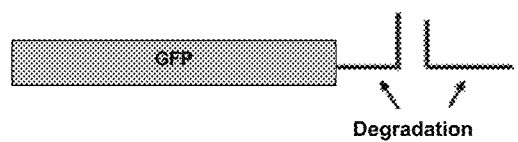

SEQUENCE LISTING

```
Sequence total quantity: 11
SEQ ID NO: 1            moltype = DNA  length = 150
FEATURE                 Location/Qualifiers
source                  1..150
                        mol_type = other DNA
                        organism = synthetic construct
SEQUENCE: 1
cctgtcggag ccaaggacag aaagctccca tagaggctgt ctccccagga attataatgc   60
ttatctactg tttccatctg tgaggtagat aagcattata attcctaggg cggcagctga  120
tggtccgccg ccggaaacag agatggctcc                                   150

SEQ ID NO: 2            moltype = DNA  length = 150
FEATURE                 Location/Qualifiers
source                  1..150
                        mol_type = other DNA
                        organism = synthetic construct
SEQUENCE: 2
cctgtcggag ccaaggacag aaagctccca aagtggctgt ggccccagga attataatgc   60
ttatctactg tttccatctg tgaggtagat aagcattata attcctaggg aggcagctca  120
aggtccgccg ccggaaacag agatggctcc                                   150

SEQ ID NO: 3            moltype = DNA  length = 181
FEATURE                 Location/Qualifiers
source                  1..181
                        mol_type = other DNA
                        organism = synthetic construct
SEQUENCE: 3
agggaatgaa gccacaggag ccaagagcag gaggaccaag gccctggcga tggccgtctc   60
```

-continued

```
ctcaggaatt ataatgctta tctatagtga agccacagat gtatagataa gcattataat    120
tcctagggcg gcggcccaga aagccggcat ccgggctcag gaccccctc tctgccagag     180
g                                                                    181

SEQ ID NO: 4          moltype = DNA    length = 173
FEATURE               Location/Qualifiers
source                1..173
                      mol_type = other DNA
                      organism = synthetic construct
SEQUENCE: 4
tctggaagcc acggagtccc atcggcacca agaccgtgtg cccctcggca ggaattataa    60
tgcttatcta tagtgaagcc acagatgtat agataagcat tataattcct actgcggggc    120
actaataact gcggtggaca gagcgtctgg aaccctggct gggagcgggc agg           173

SEQ ID NO: 5          moltype = DNA    length = 154
FEATURE               Location/Qualifiers
source                1..154
                      mol_type = other DNA
                      organism = synthetic construct
SEQUENCE: 5
tcgaaagaga ttgtactttc cattccagaa gacaacctgg ctctctccgc aggaattata    60
atgcttatct atagtgaagc cacagatgta tagataagca ttataattcc tatggcgaga    120
gcccttgctg cattattttc tttttattta gatg                                154

SEQ ID NO: 6          moltype = DNA    length = 163
FEATURE               Location/Qualifiers
source                1..163
                      mol_type = other DNA
                      organism = synthetic construct
SEQUENCE: 6
gatagttccg agtagctggc ccacataggc tgaagatagc cccttgtgct actcggcagg    60
aattataatg cttatctata gtgaagccac agatgtatag ataagcatta taattcctac    120
cgcgtggtac tcttcttctc cgactggctc tgttcaggtt ctt                      163

SEQ ID NO: 7          moltype = DNA    length = 154
FEATURE               Location/Qualifiers
source                1..154
                      mol_type = other DNA
                      organism = synthetic construct
SEQUENCE: 7
ccgtgctgtg ctccctcgcc ccaccctgcc cggctcccca ggaattataa tgcttatcta    60
tagtgaagcc acagatgtat agataagcat tataattcct agggcgccgg gcccccctg    120
ccttggggtg aggggctgc ccctggattc ctgc                                154

SEQ ID NO: 8          moltype = DNA    length = 194
FEATURE               Location/Qualifiers
source                1..194
                      mol_type = other DNA
                      organism = synthetic construct
SEQUENCE: 8
tgccatattt ggaggagctg actgaagata tgataaggag tttgaagcaa cattggaaaa    60
ttggtggact cggcaggaat tataatgctt atctatagtg aagccacaga tgtatagata    120
agcattataa ttcctattgc gtccaccttc aagcgtcgag gaattcttca tcactttaac    180
ctgattgagc caat                                                      194

SEQ ID NO: 9          moltype = DNA    length = 194
FEATURE               Location/Qualifiers
source                1..194
                      mol_type = other DNA
                      organism = synthetic construct
SEQUENCE: 9
ataagactaa cttgtaattt ccctgcttaa gaaatggtag ttttccagcc attgagactt    60
gatgctctca gcaggaatta taatgcttat ctatagtgaa gccacagatg tatagataag    120
cattataatt cctattgcga gcatccctaa acaacatggt gagaacgatc atgattcctc    180
caggccttt ctcc                                                       194

SEQ ID NO: 10         moltype = DNA    length = 129
FEATURE               Location/Qualifiers
source                1..129
                      mol_type = other DNA
                      organism = synthetic construct
SEQUENCE: 10
accattcacc ctgatgttc tcttcactgt ggcaggaatt ataatgctta tctatagtga    60
agccacagat gtatagataa gcattataat tcctactaac gtgatagaaa agtctgcatc    120
caggcggtc                                                            129

SEQ ID NO: 11         moltype = DNA    length = 174
FEATURE               Location/Qualifiers
source                1..174
```

```
                    mol_type = other DNA
                    organism = synthetic construct
SEQUENCE: 11
tctggaagcc acggagtccc atcggcacca agaccgactg ccctttggca ggaattataa    60
tgcttatcta tagtgaagcc acagatgtat agataagcat tataattcct actgaagtgg   120
ctgtaatatc tgcggtggac agagcgtctg gaaccctggc tgggagcggg cagg         174
```

COMPOSITIONS AND METHODS OF GENERATING NOVEL amiRNA

CROSS-REFERENCE TO RELATED APPLICATIONS

The present applications claims priority to PCT application serial no. PCT/US2023/012483, filed Feb. 7, 2023, which claims priority to U.S. provisional application Ser. No. 63/325,207, filed Mar. 30, 2022, each incorporated by reference in its entirety.

SEQUENCE LISTING

The present application contains a Sequence Listing which is submitted electronically in XML format and is incorporated by reference in its entirety. Said XML file was created on Feb. 7, 2023, is named XML Sequence MIS-105-US-CON.xml and 12,321 bytes in size.

BACKGROUND

The invention generally relates to amiRNA (artificial microRNA) technology.

RNA interference (RNAi) is a biological process in which the expression of a given gene is inhibited by small complementary RNAs. One class of such small RNAs is called microRNAs (miRNAs), and it is responsible for the silencing of hundreds of thousands of genes in all known Eukaryotic organism. miRNAs are derived from the processing of primary miRNAs by specific cellular enzymatic complexes.

The major components of a given primary miRNA are the scaffold and the guide/passenger. The scaffold is further categorized into Base, Basal Stem and Loop. Specific structures and nucleotide sequences in such regions regulates the efficiency and precision of the processing of the primary-miRNA into miRNA and subsequent potency of silencing of the target messenger RNA (mRNA).

The Guide/Passenger region is responsible for the targeting of a specific mRNA. The Guide/Passenger region, for most of the cases, is equivalent the mature miRNA (aka miRNA-miRNA* duplex). A schematic of the processing from primary miRNA to miRNA is depicted in FIG. 1. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease in the cytoplasm to generate the mature miRNA (Guide) and antisense miRNA star (miRNA) products. The mature miRNA (Guide) is incorporated into a RNA-induced silencing complex (RISC), which recognizes target mRNAs through imperfect base pairing with the miRNA and most commonly results in translational inhibition or destabilization of the target mRNA (mRNA targeting).

The rationale behind the generation of amiRNA is to create RNAi molecules with an enhanced potency that can potentially target any RNA in cells. The processing and targeting process are adjuvated by enzymatic complexes that are already present in every cell (unlike other approaches for modulation of gene expression such as CRISPR/Cas9), making the building of a therapeutic more feasible and safer. Moreover, amiRNAs can be expressed from a RNA Polymerase II promoter, resulting in less cytotoxic effects.

Current methods to generate amiRNA constructs can be tedious and cost- and time-ineffective for high-throughput applications.

The present invention attempts to solve these problems, as well as others.

SUMMARY OF THE INVENTION

Provided herein are methods for producing or generating one or more amiRNAs; also provided are constructs and compositions useful in the methods. The methods and constructs provided in this disclosure are highly efficient methods for production of a new generation of amiRNAs.

The methods and compositions are set forth in part in the description which follows, and in part will be obvious from the description, or can be learned by practice of the methods and compositions. The advantages of the methods and compositions will be realized and attained by means of the elements and combinations particularly pointed out in the appended claims. It is to be understood that both the foregoing general description and the following detailed description are exemplary and explanatory only and are not restrictive of the methods and compositions, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

FIG. 2B is a table showing the values of the residule fluorescence of the amiRNAs and the corresponding averages.

FIG. 3A is a schematic showing the selected primary miRNAs to be modified in specific regions of Endogenous Let7a1; and FIG. 3B is a schematic showing the selected primary miRNAs modified in specific regions of amiRNA Let7a1 to obtain novel miRNA.

FIG. 7 is a schematic diagram of DROSHA processing for the GFP-amiRNA hybrid transcribed from the rAAV.

DETAILED DESCRIPTION OF THE INVENTION

Figure 1:
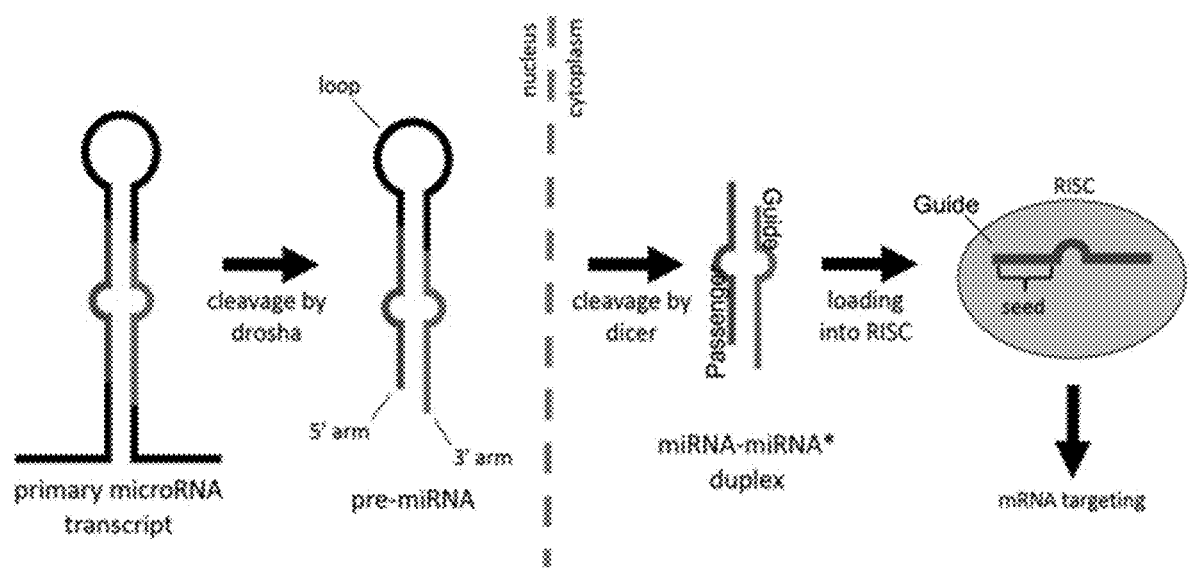
FIG. 1 is a schematic of the Biosynthetic pathway from primary miRNA to miRNA.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Definitions

As used herein, "nucleic acid" means a polynucleotide (or oligonucleotide) and includes single or double-stranded polymer of deoxyribonucleotide or ribonucleotide bases, and unless otherwise limited, encompasses known analogues having the essential nature of natural nucleotides in that they hybridize to single-stranded nucleic acids in a manner similar to naturally occurring nucleotides (e.g., peptide nucleic acids). Nucleic acids may also include fragments and modified nucleotides.

As used herein, "nucleic acid construct" or "construct" refers to an isolated polynucleotide which is introduced into a host cell. This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used herein, "microRNA" (also referred to herein interchangeable as "miRNA" or "miR") refers to an oligoribonucleic acid, which regulates the expression of a polynucleotide comprising the target sequence transcript. Typically, microRNAs (miRNAs) are noncoding RNAs of approximately 21 nucleotides (nt) in length that have been identified in diverse organisms, including animals and plants (Lagos-Quintana et al., Science 294:853-858 2001, Lagos-Quintana et al, Curr. Biol. 12:735-739 2002; Lau et al, Science 294:858-862 2001; Lee and Ambros, Science 294: 862-864 2001; Llave et al., Plant Cell 14:1 605-1619 2002; Mourelatos et al., Genes. Dev. 16:720-728 2002; Park et al., Curr. Biol. 12:1484-1495 2002; Reinhart et al, Genes. Dev. 16:1616-1626 2002). Primary transcripts of miRNA genes form hairpin structures that are processed by the multidomain RNases DICER and DROSHA (in animals) or DICER-LIKE1 (DCL1; in plants) to yield miRNA duplexes. As used herein "pre-microRNA" refers to these miRNA duplexes, wherein the foldback includes a "distal stem-loop" or "distal SL region" of partially complementary oligonucleotides, "mature miRNA" refers to the miRNA which is incorporated into RISC complexes after duplex unwinding. In one embodiment, the miRNA is the region comprising R] to Rn, wherein "n" corresponds to the number of nucleotides in the miRNA. In another embodiment, the miRNA is the region comprising R'i to R'n, wherein "n" corresponds to the number of nucleotides in the miRNA. In one aspect, "n" is in the range of about from 15 to about 25 nucleotides, in another aspect, "n" is about 20 or about 21 nucleotides. The term miRNA is specifically intended to cover naturally occurring polynucleotides, as well as those that are recombinantly or synthetically or artificially produced, or amiRNAs.

A "small interfering RNA" or "siRNA" means RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity. The term siRNA is specifically intended to cover naturally occurring oligonucleotides, as well as those that are recombinantly or synthetically produced.

The term "silencing" or "silencing molecule" as used herein means a specific molecule, which can exert an influence on a cell in a sequence-specific manner to reduce or silence the expression or function of a target, such as a target gene or protein. Examples of silence agents include nucleic acid molecules such as naturally occurring or synthetically generated small interfering RNAs (siRNAs), naturally occurring or synthetically generated microRNAs (miR-NAs), naturally occurring or synthetically generated dsRNAs, and antisense sequences (including antisense oligonucleotides, hairpin structures, and antisense expression vectors), as well as constructs that code for any one of such molecules.

The term "RNAi potency or amiRNA potency" as used here in refers to the RNAs ability to interfere or inhibit the expression of a target sequence. RNAi potency refers to the ability of a small RNA, or other molecule, to measurably reduce the expression and/or stability of molecules carrying the target sequence. "Interfering" or "inhibiting" expression contemplates reduction of the end-product of the gene or sequence, e.g., the expression or function of the encoded protein or a protein, nucleic acid, other biomolecule, or biological function influenced by the target sequence, and thus includes reduction in the amount or longevity of the mRNA transcript or other target sequence. In some embodiments, the small RNA or other molecule guides chromatin modifications which inhibit the expression of a target sequence. It is understood that the phrase is relative, and does not require absolute inhibition (suppression) of the sequence. Thus, in certain embodiments, interfering with or inhibiting expression of a target sequence requires that, following application of the small RNA or other molecule (such as a vector or other construct encoding one or more small RNAs), the target sequence is expressed at least 5% less than prior to application, at least 10% less, at least 15% less, at least 20% less, at least 25% less, or even more reduced. Thus, in some particular embodiments, application of a small RNA or other molecule reduces expression of the target sequence by about 30%, about 40%, about 50%, about 60%, or more. In specific examples, where the small RNA or other molecule is reduces expression of the target sequence by 70%, 80%, 85%, 90%, 95%, or even more.

As used herein, the phrases "target sequence", "targeting a gene", and "sequence of interest" are used interchangeably and encompass DNA, RNA (comprising pre-mRNA and mRNA) transcribed from such DNA, and also cDNA derived from such RNA, and may also refer to a polynucleotide comprising the target sequence. Target sequence is used to mean the nucleic acid sequence that is selected for suppression of expression, and is not limited to polynucleotides encoding polypeptides. Target sequences may include coding regions and non-coding regions such as long non-coding RNAs, promoters, enhancers, terminators, introns and the like. The target sequence may be an endogenous sequence, or may be an introduced heterologous sequence, or transgene. The specific hybridization of an oligomeric compound with its target sequence interferes with the normal function of the nucleic acid. The target sequence comprises a sequence that is substantially or completely complementary between the oligomeric compound and the target sequence. This modulation of function of a target nucleic acid by compounds, which specifically hybridize to it, is generally referred to as "antisense".

As used herein "operably linked" refers to a functional arrangement of elements. A first nucleic acid sequence is operably linked with a second nucleic acid sequence when the first nucleic acid sequence is placed in a functional relationship with the second nucleic acid sequence. In specific embodiments, operably linked nucleic acids as discussed herein are aligned in a linear concatamer capable of being cut into fragments, at least one of which is a small RNA molecule.

As used herein, the phrase "sequence identity" or "sequence similarity" is the similarity between two (or more) nucleic acid sequences, or two (or more) amino acid sequences, is expressed in terms of the similarity between the sequences, otherwise referred to as sequence identity or sequence homology. Sequence identity is frequently measured as the percent of identical nucleotide or amino acid residues at corresponding positions in two or more sequences when the sequences are aligned to maximize sequence matching, i.e., taking into account gaps and insertions.

One of ordinary skill in the art will appreciate that these sequence identity ranges are provided for guidance only; it is entirely possible that strongly significant similarity could be obtained that fall outside of the ranges provided. Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein. Means for making this adjustment are well-known to those of skill in the art. When percentage of sequence identity is used in reference to amino acid sequences it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity.

Description of Embodiments

Artificial miRNAs (amiRNAs) are important and promising tools for the development of novel targeted therapeutics. However, just a few amiRNAs are available to the scientific community. Generally speaking, the method of generating amiRNAs comprises optimizing miRNA processing and miRNA potency. In one embodiment, the composition of amiRNAs includes a miRNA potency higher than the gold standard amiRNAs miRE and miR155. A decrease in fluorescence in a miRNA potency assay is directly proportional to potency. The mean value for the potency is represented by a percentage of the target that is reduced compared to a control with no amiRNA and includes: miR155 at about 65.86%, miRE at about 68.12%, Let7a3_Loop at about 70.51%, Let7a1_Loop at about 75.54%, Let7a2_All at about 75.93%, Let7c_All at about 76.10%, miR26b_All at about 76.38%, Let7f2_All at about 76.91%, Let7f1_All at about 77.18%, Let7a3_All at about 78.18%, miR26a1_All at about 78.31%, miR26a2_Base at about 80.28%, and miR26a2_Stem at about 80.50%.

The amiRNAs can be modified by creating hybrid constructs of the Base region, the Basal Stem region, and the Loop region from different endogenous and modified primary miRNAs. Experimental validation may investigate if the function remains intact or not. Artificial miRNAs (amiRNAs) disclosed herein may be used as RNA Therapeutics, according to one embodiment. Experimental validation includes transgenic animal models that a) exhibited the expected phenotypes predicted by loss of target gene function, b) accumulated high levels of accurately processed amiRNAs, or c) had reduced levels of the corresponding target RNAs.

In one embodiment, the method of generating amiRNAs comprises modifying specific regions of a primary miRNA to increase the silencing potency and to target a given mRNA of interest. In one embodiment, the method comprises selecting a set of miRNAs with high expression rate according to a miRNAs database including miRbase (https://www.mirbase.org/). The method comprises obtaining the sequence of the corresponding primary miRNAs, and selecting between about 100 to about 200 nucleotides of each primary miRNA according to the conservation tool. In one embodiment, the conservation tool includes the "Cons 100 Verts" tool in the USCS Genome Browser (http://genome.ucsc.edu/). Then, the method comprises modifying the selected primary miRNAs in specific regions including a base region, a basal stem region, and a loop region.

The base modifying step produces a single stranded region of at least 9 nucleotides and a GU dinucleotide in position −13 and −14 respectively from a Drosha cleavage site. Drosha cleavage site is for Drosha ribonuclease III. The base modifying step entails the mutation of nucleotides in a manner to result in an intended structure for the base. The intended structures resulting from the base modifying step are checked using a RNA folding webserver tool In one embodiment, the RNA folding webserver tool is selected from http://rna.tbi.univie.ac.at/cgi-bin/RNA WebSuite/RNAfold.cgi.

The basal stem step modifying produces a double stranded RNA with a CHC motif and a bulge in position +8 from Drosha cleavage site. In one embodiment, the total length of the modified basal stem is 11 base pairs or between 9 to 13 base pairs, wherein the optimal length being 11 base pairs. The basal stem modifying step entails the mutation of nucleotides in a manner to result in the intended structure of the basal stem. The structures resulting from the basal stem modifying step are checked using the RNA folding webserver tool.

The loop modifying step entails the substitution of the endogenous loop region of the primary miRNA with the loop of miRE, an amiRNA or another loop with same number of nucleotides and the GUG motif in the same position. The structures resulting from the modifications were checked using the RNA folding webserver tool (http://rna.tbi.univie.ac.at/cgi-bin/RNA WebSuite/RNAfold.cgi).

The base modified construct, the basal stem modified construct, and the loop modified construct are operably linked into one amiRNA construct with the primary miRNA. The combination of the base modifying step, the basal stem modifying step, and the loop modifying step result in amiRNAs with an enhanced silencing potency. FIGS. 3A-3B shows the base modified construct, the basal stem modified construct, and the loop modified construct with the primary miRNA Let7a1 to obtain the novel amiRNA Let7a1_All.

The method of generating Artificial miRNAs 200 (amiRNAs) comprises modifying an endogenous primary-miRNAs gene 100, as shown in FIGS. 3A-3B. Modifying endogenous primary mi-RNA occurs in the loop region 110, the basal stem region 114, and the base region 116, while the guide/passenger region 112 may or may not change. As shown in FIG. 3B, the loop modifying step 210 includes increasing precision and efficiency of DICER processing. Dicer ribonuclease to generate the mature miRNA. The Guide/Passenger step 212 includes targeting a specific gene or target sequence. The basal stem step 214 includes increasing the precision and efficiency of DICER processing. The base step 216 includes increasing the precision and efficiency of DROSHA processing.

The modifications at the nucleotide level, are based on known structural determinants that generate more powerful tools for RNA-mediated gene silencing.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Figure 2A:
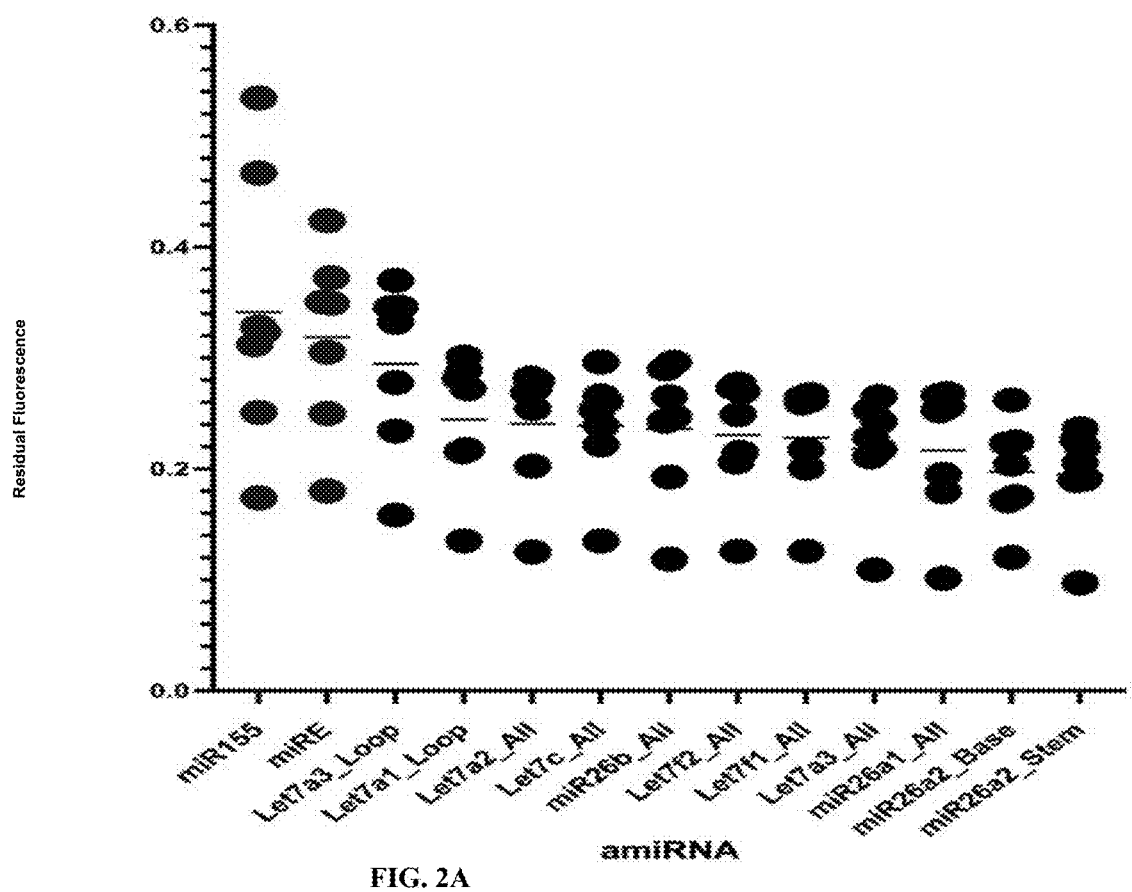
FIG. 2A is a graph showing the silencing assay to evaluate the potency of the novel scaffolds in comparison to miRE and miR155. The higher is the potency of the amiRNA, the lower will be the residual fluorescence.

To validate the method of generating novel amiRNAs, silencing experiments were performed comparing the potency of the novel amiRNAs with the known and extensively used amiRNAs miRE and miR155. The experiment is based on the targeting of fluorescent gene with the amiRNAs; the decreasing in fluorescence is directly proportional to the potency of the amiRNA. As shown in FIGS. 2A-2B, the novel amiRNAs cause a higher decrease in fluorescent gene expression, ranking them as more potent than miRE and miR155.

Sequences:

The sequences are heterologous or synthetic or artificial single-stranded ribonucleic acid (RNA) comprising (i) a selected primary miRNA and the complement thereof, and (ii) a base region in between the selected primary miRNA and the complement thereof, wherein the nucleotide sequence of the base region is at least 75% sequence identity to SEQ ID NO: 1.

The heterologous or synthetic or artificial single-stranded ribonucleic acid (RNA) sequence may comprise (i) a selected primary miRNA and a complement thereof, and (ii) a base region and a basal stem in between the selected primary miRNA and a loop region, wherein the nucleotide sequence of the base region, the base stem region, and the loop region is at least 75% sequence identity to SEQ ID NOs: 3-9.

In accordance with another embodiment, the nucleotide sequence identity of the base region, the base stem region, and the loop region is at least 70%, is at least 75%, is at least 80%, is at least 85%, is at least 90%, is at least 95%, is at least 97%, is at least 99% to SEQ ID NOs: 3-9.. In accordance with another embodiment of the invention, the nucleotide sequence identity of the loop region is at least 75% sequence identity to SEQ ID Nos: 10-11.

In accordance with another embodiment, the nucleotide sequence is identical or 100% sequence identity to SEQ ID NOs: 1-11.

In one embodiment, the sequences of the novel amiRNAs are listed below. The lower-case nucleotides are the modifications implemented to obtain the intended structures. The green labelled sequences are the Guide/Passenger duplex; such region can be changed to target virtually any mRNA or RNA transcript.

```
miR26a2_Stem:
                                                                         SEQ ID NO: 1
CCTGTCGGAGCCAAGGACAGAAAGCTCCCATAGAGGCTGTctCcccaggaattataatg cttatctaCTGTTTCCATCTGTGAGGtagataagcattataattcctagGGcGGCAGCTGATGGTCCGCCG

CCGGAAACAGAGATGGCTCC miR26a2_Base:
                                                                         SEQ ID NO: 2
CCTGTCGGAGCCAAGGACAGAAAGCTCCCAaAGtGGCTGTGGCcccaggaattataatg cttatctaCTGTTTCCATCTGTGAGGtagataagcattataattcctagGGAGGCAGCTcAaGGTCCGCCG

CCGGAAACAGAGATGGCTCC miR26a1_All:
                                                                         SEQ ID NO: 3
AGGGAATGAAGCCACAGGAGCCAAGAGCAGGAGGACCAAGGCCCTGGCGAt

GGCCGTctCCTcaggaattataatgcttatctatagtgaagccacagatgtatagataagcattataattcctaGGGCgGCGGc CCaGaAaGCCGGCATCCGGGCTCAGGACCCCCCTCTCTGCCAGAGG Let7a3_All:
                                                                         SEQ ID NO: 4
TCTGGAAGCCACGGAGTCCCATCGGCACCAAGACCGtgTGCCCcTcGGcaggaattat aatgcttatctatagtgaagccacagatgtatagataagcattataattcctaCTGcgGgGcacTAATAaCTGCGGTGGAC

AGAGCGTCTGGAACCCTGGCTGGGAGCGGGCAGG

Let7f1_All:
                                                                         SEQ ID NO: 5
TCGAAAGAGATTGTACTTTCCATTCCAGAAGAcAACcTgGCTCTcTCcGcaggaatta taatgcttatctatagtgaagccacagatgtatagataagcattataattcctaTGgcGAGagccCTTGCTGCATTATTTTC

TTTTTATTTAGATG
```

Let7f2_All:

SEQ ID NO: 6

GATAGTTCCGAGTAGCTGGCCCACATAGGCTGAAGATaGcCcCTtGTGCTactcG

GcaggaattataatgcttatctatagtgaagccacagatgtatagataagcattataattcctaCcgcGTGGTACtCTTCTTCTC

CGACTGGCTCTGTTCAGGTTCTT miR26b_All:

SEQ ID NO: 7

CCGTGCTGTGCTCCCTCGCCCCACCCTGcCCGGctCCCcaggaattataatgcttatctatagtga agccacagatgtatagataagcattataattcctagGGcGcCgGgcCCCccCtGCCTTGGGGTGAGGGGGCTGC

CCCTGGATTCCTGC

Let7c_All:

SEQ ID NO: 8

TGCCATATTTGGAGGAGCTGACTGAAGATATGATAAGGAGTTTGAAGCAACA

TTGGAAaaTtgGTGgActCGGcaggaattataatgcttatctatagtgaagccacagatgtatagataagcattataattcctaTT GcgtCcacCTTcAagCGTCGAGGAATTCTTCATCACTTTAACCTGATTGAGCCAAT Let7a2_All:

SEQ ID NO: 9

ATAAGACTAACTTGTAATTTCCCTGCTTAAGAAATGGTAGTTTTCCAGCCATT

GaGACTtgATGCTCtCAGcaggaattataatgcttatctatagtgaagccacagatgtatagataagcattataattcctaTTGc GagcatCcCTAAACAACATGGTGAGAACGATCATGATTCCTCCAGGCCTTTTCTCC Let7a1_Loop:

SEQ ID NO: 10

ACCATTCACCCTGGATGTTCTCTTCACTGTGGcaggaattataatgcttatctatagtgaagccaca gatgtatagataagcattataattcctaCTAACGTGATAGAAAAGTCTGCATCCAGGCGGTC Let7a3_Loop:

SEQ ID NO: 11

TCTGGAAGCCACGGAGTCCCATCGGCACCAAGACCGACTGCCCTTTGGcaggaat tataatgcttatctatagtgaagccacagatgtatagataagcattataattcctaCTGAAGTGGCTGTAATATCTGCGG

TGGACAGAGCGTCTGGAACCCTGGCTGGGAGCGGGCAGG

Example 2: Novel Artificial amiRNA Supplemental Experimental Validation GM

Figure 4:
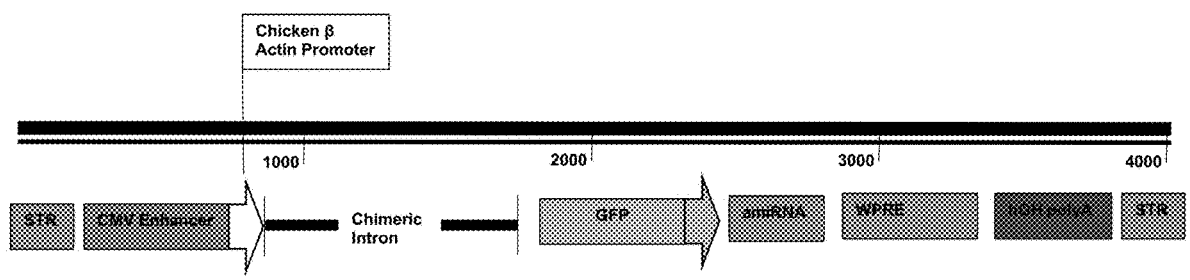
FIG. 4 is a schematic of the recombinant rAAV for the delivery of amiRNAs in a therapeutical setting. The GFP-amiRNA transcription is driven by the ubiquitous CAGG promoter.

In order to further confirm the efficiency of the novel amiRNAs in a system that resembles more a therapeutical setting, the scaffolds were delivered using rAAV vectors in Human Induced Pluripotent Stem Cells (hIPSC)-derived NGN2 Neurons in vitro. A schematic of the viral vectors is shown in FIG. 4.

The amiRNAs were loaded with a Guide/Passenger duplex targeting the gene PTEN, but as mentioned before, virtually any gene could be targeted.

Following rAAV infection, RNA and proteins from NGN2 neurons were collected to assess: Knockdown levels of PTEN at the protein level; Knockdown levels of PTEN at the RNA level; amiRNA processing rate through quantification of residual GFP transcript; amiRNA processing precision through small-RNA sequencing; Guide/Passenger ratio through small-RNA sequencing.

Figure 5:
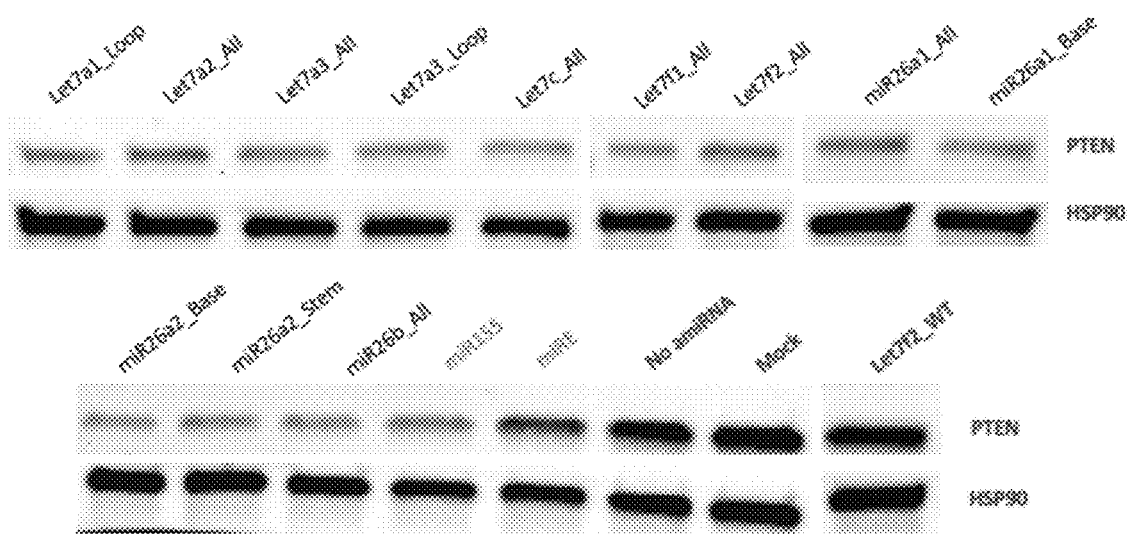
FIG. 5 is a western Blot experiment showing the decreasing in PTEN protein levels due to the expression of amiRNAs targeting the same. Three negative controls are included in the experiment: No amiRNA are cells infected with a virus expressing GFP but no amiRNA; Mock are untreated cells; Let7f2_WT are cells infected with an unmodified amiRNA already know to not cause any knockdown. Image representative of three independent experiments. HSP90 is shown as loading control

FIG. 5 shows how the expression of all the novel amiRNAs causes a similar or stronger knockdown of PTEN protein compared to miRE and miR155.

Knockdown Levels of PTEN at the RNA Level

Quantitative Polymerase Chain Reaction (qPCR) shows how the expression of all the novel amiRNAs causes a similar or stronger knockdown of PTEN mRNA compared to miRE and miR155. The results are shown in Table 1 below and FIG. 6.

TABLE 1

| mRNA | Construct | n1 | n2 | n3 | Average | ST. DEV. |
|---|---|---|---|---|---|---|
| PTEN | miR155 | 0.3588212 | 0.8859063 | 0.20832285 | 0.4843501 | 0.3558061 |
| PTEN | miRE | 0.5696833 | 0.7137689 | 0.49780797 | 0.5937534 | 0.1099741 |
| PTEN | Let7a1Loop | 0.3554444 | 0.3788072 | 0.44323799 | 0.3924965 | 0.0454695 |
| PTEN | Let7a2All | 0.4970672 | 0.7636191 | 0.33305910 | 0.5312485 | 0.2173056 |
| PTEN | Let7a3All | 0.3015426 | 0.2899735 | 0.18795147 | 0.2598225 | 0.0625103 |
| PTEN | Let7a3Loop | 0.3868847 | 0.3855019 | 0.32351912 | 0.3653019 | 0.0361915 |
| PTEN | Let7cAll | 0.3382417 | 0.3588942 | 0.52827321 | 0.4084697 | 0.1042654 |
| PTEN | Let7f1All | 0.3103382 | 0.3027810 | 0.41917458 | 0.3440979 | 0.0651279 |
| PTEN | Let7f2All | 0.3616355 | 0.6188231 | 0.31349537 | 0.4313180 | 0.1641584 |
| PTEN | miR26a1All | 0.3262570 | 0.6415056 | 0.09331101 | 0.3536912 | 0.2751250 |

TABLE 1-continued

| mRNA | Construct | n1 | n2 | n3 | Average | ST. DEV. |
|---|---|---|---|---|---|---|
| PTEN | miR26a1Bas | 0.3336085 | 0.3019544 | 0.17008942 | 0.2685508 | 0.0867264 |
| PTEN | miR26a2Bas | 0.2631133 | 0.2432865 | 0.09335516 | 0.1999183 | 0.0928173 |
| PTEN | miR26a2Ste | 0.3598046 | 0.6709461 | 0.13055743 | 0.3871027 | 0.2712266 |
| PTEN | miR26bAll | 0.6727930 | 0.2528890 | 0.19377922 | 0.3731537 | 0.2611728 |
| PTEN | Let7f2WT | 0.9624846 | 1.4845724 | 0.78453175 | 1.0771962 | 0.3638451 |
| PTEN | no amiRNA | 1 | 1 | 1 | 1 | 0 |
| PTEN | Mock | 1.2040792 | 1.4804738 | 1.07503209 | 1.2531950 | 0.2071352 |

Figure 6:
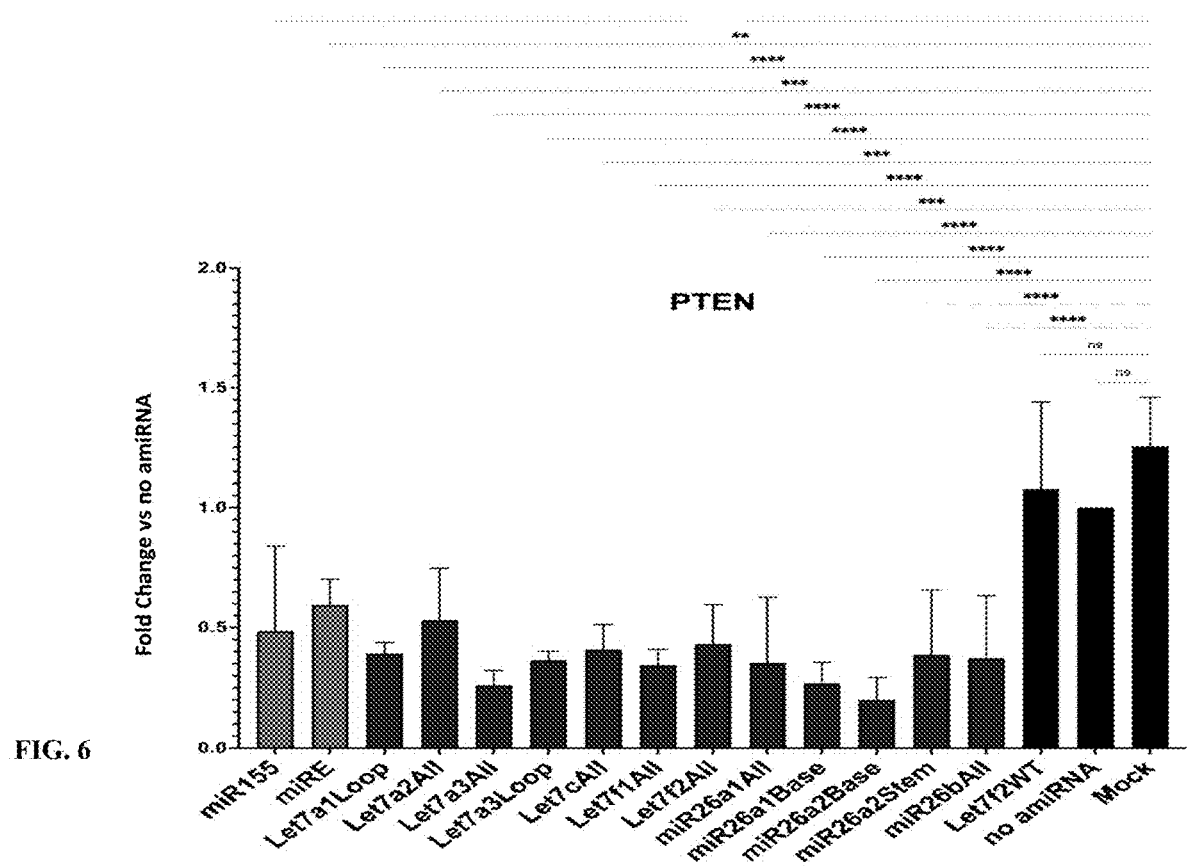
FIG. 6 is a graph showing the qPCR experiment and the decreasing in PTEN transcripts levels due to the expression of amiRNAs targeting the same. Three negative controls are included in the experiment: No amiRNA are cells infected with a virus expressing GFP but no amiRNA; Mock are untreated cells; Let7f2_WT are cells infected with an unmodified amiRNA already know to not cause any knockdown. The average of three independent biological replicates is plotted; error bars represent Standard Deviation; t-test was implemented to derive the p-value vs "Mock" sample.

As shown in FIG. 6, qPCR experiment showing the decreasing in PTEN transcripts levels due to the expression of amiRNAs targeting the same. Three negative controls are included in the experiment: No amiRNA are cells infected with a virus expressing GFP but no amiRNA; Mock are untreated cells; Let7f2_WT are cells infected with an unmodified amiRNA already know to not cause any knockdown. The average of three independent biological replicates is plotted; error bars represent Standard Deviation; t-test was implemented to derive the p-value vs "Mock" sample.

amiRNA Processing Rate Through Quantification of Residual GFP Transcript

The amiRNAs are transcribed downstream of the GFP gene creating a GFPmRNA-amiRNA hybrid transcript. Following DROSHA processing, the amiRNA gets processed in the canonical miRNA biogenesis pathway (export into cytoplasm, DICER processing, loading of the guide strand into RISC complex and target silencing). Oppositely, the GFP portion of the transcript gets quickly degraded by cellular nucleases, as shown in FIG. 7.

Figure 8:
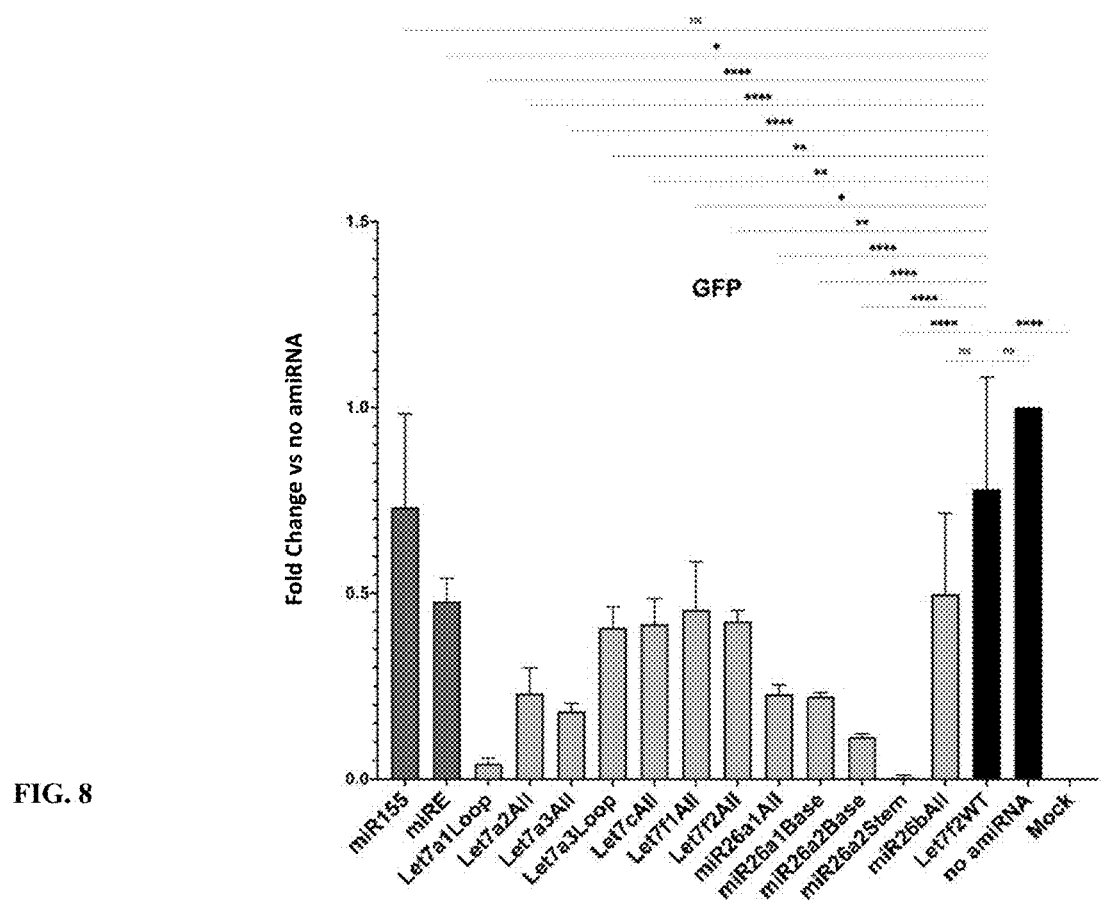
FIG. 8 is a graph showing the qPCR experiment and the decreasing in GFP transcripts levels due to DROSHA processing of the amiRNAs. Three negative controls are included in the experiment: No amiRNA are cells infected with a virus expressing GFP but no amiRNA; Mock are untreated cells; Let7f2_WT are cells infected with an unmodified amiRNA already known to not cause any knockdown. The average of three independent biological replicates is plotted; error bars represent Standard Deviation; t-test was implemented to derive the p-value vs "Let7f2 WT" sample.

Therefore, quantification of the residual GFP transcript is an indicator of how efficiently a given amiRNA is processed by DROSHA. High DROSHA processing ensures high downstream levels of mature miRNA which eventually result in higher knockdown efficiency. FIG. 8 and Table 2 shows the qPCR data for the quantification of residual GFP transcript; data indicate that the novel amiRNAs are, in most of the cases, processed more efficiently than miRE and miR155.

amiRNA Processing Precision Through Small-RNA Sequencing

An important feature of a powerful amiRNA is the precision of the processing by DROSHA and DICER. Indeed, unprecise processing may result in variable 5' ends of the guide and passenger strands with resulting off targeting and/or loading of the passenger strand into RISC. Small-RNA seq were employed to study this important aspect of amiRNAs processing and as shown in the figures contained in "Processing Precision" file, all the novel amiRNAs are precisely processed with >95% of the guide strands starting on the correct 5' nucleotide. Importantly, the negative control Letf2WT shows a dramatic decreasing of mature guides starting on the correct 5' nucleotide, pointing out the difference from the highly efficient scaffolds.

Guide/Passenger Ratio Through Small-RNA Sequencing

Figure 9A:
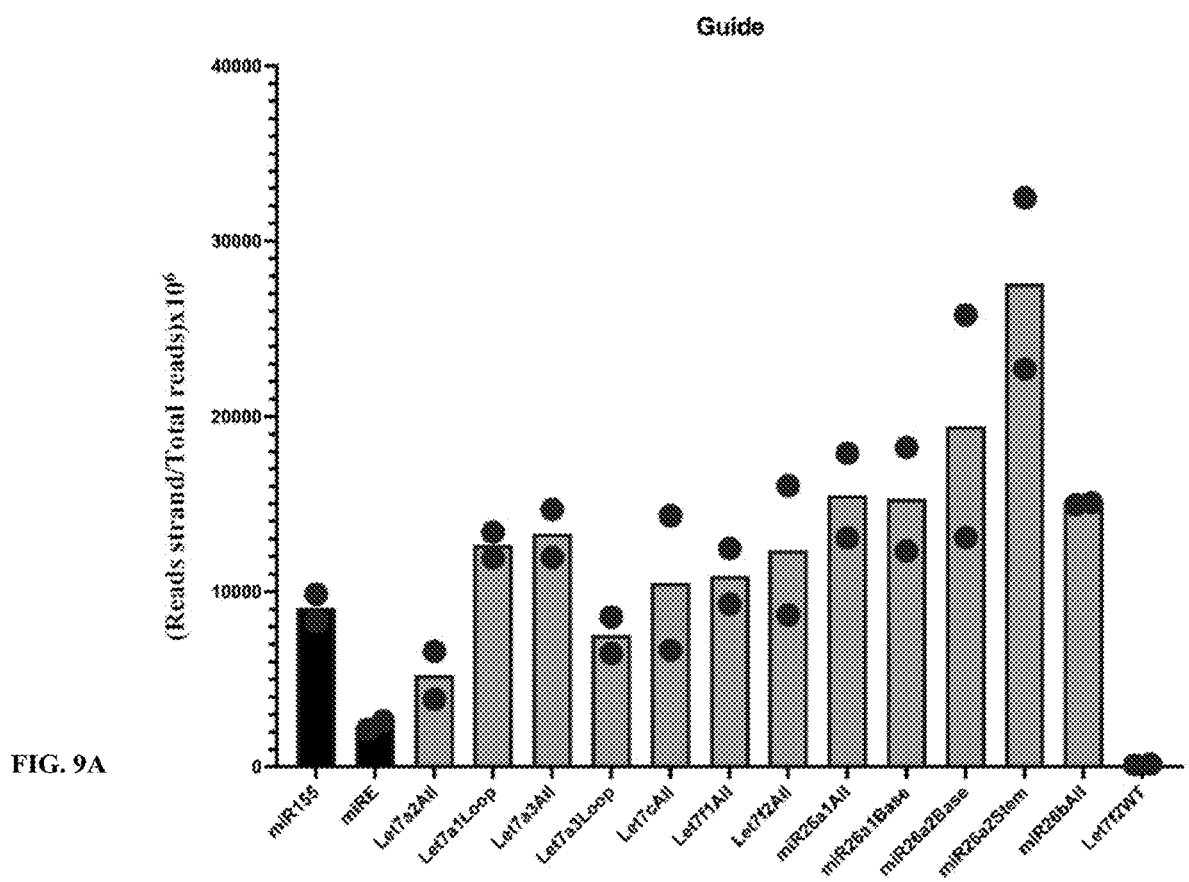
FIGS. 9A-9B are graphs showing the normalized Quantification of Guide and Passenger strand derived from the novel amiRNAs. As highlighted by the difference Y-axis scales, the amount of Guide strand is far higher than that of the Passenger strand.
Figure 9B:
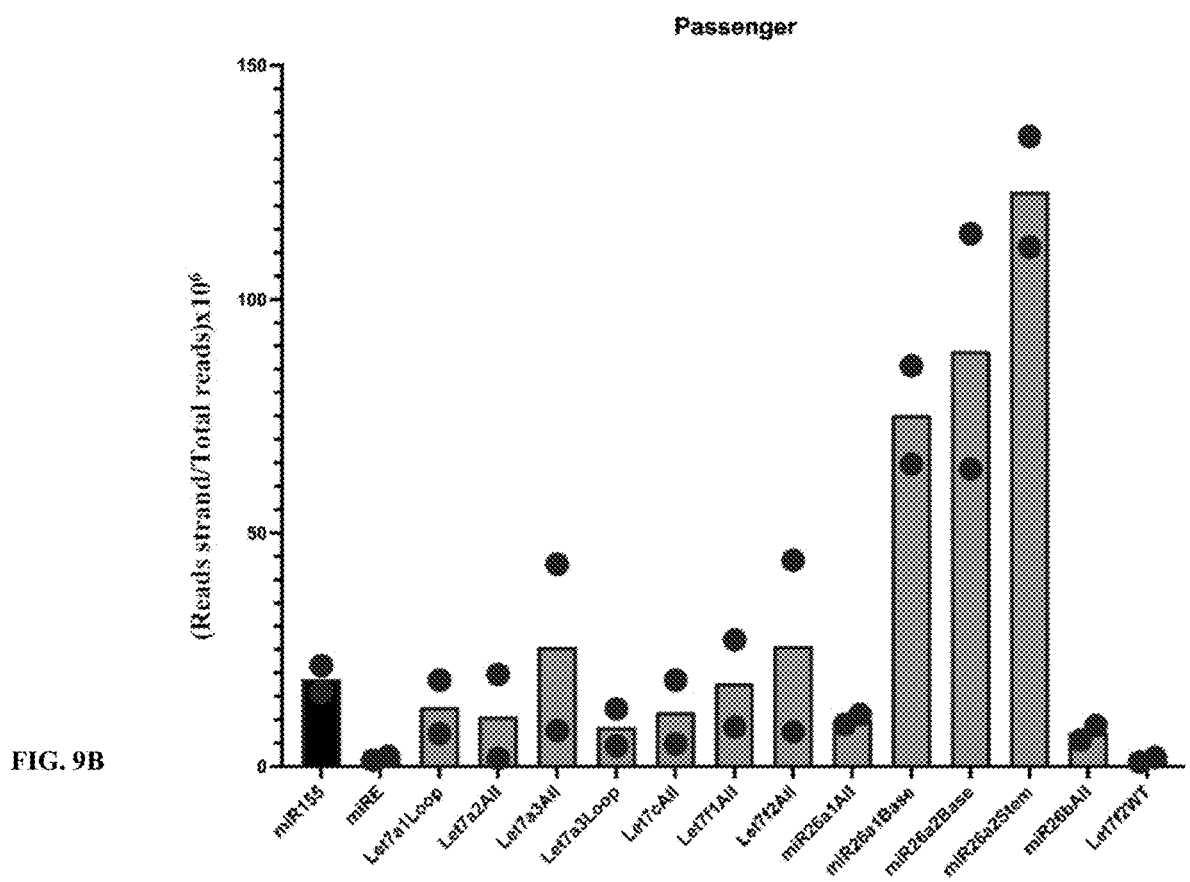

Following DROSHA and DICER processing, only the Guide strand should be loaded on RISC complex; the Passenger strand instead gets quickly degraded. In the case of amiRNAs, it is important to make sure that high amount of Guide strand is detectable in contrast to Passenger strand that should be detectable in far less copies. This aspect was assessed through small-RNA seq and while the Guide strand is detected at a magnitude of thousands to tens of thousands more abundant that the Passenger amount, which is several folds lower with amount topping at a few thousands reads only, as shown in the normalized data in Table 3 and FIGS. 9a and 9b. This data supplements and confirms the previous data of knockdown efficiency and processing precision and efficacy.

TABLE 2

| mRNA | Construct | n1 | n2 | n3 | Average | ST. DEV. |
|---|---|---|---|---|---|---|
| GFP | miR155 | 0.7127257 | 0.6762464 | 0.62683733 | 0.6719365 | 0.0431061 |
| GFP | miRE | 0.2855355 | 0.3119356 | 0.30245356 | 0.2999749 | 0.0133734 |
| GFP | Let7a1Loop | 0.2063730 | 0.2605471 | 0.19203894 | 0.2196530 | 0.0361332 |
| GFP | Let7a2All | 0.3612918 | 0.4041511 | 0.28178316 | 0.3490753 | 0.0620919 |
| GFP | Let7a3All | 0.4822237 | 0.5156252 | 0.48856145 | 0.4954701 | 0.0177401 |
| GFP | Let7a3Loop | 0.5827107 | 0.5976963 | 0.46632488 | 0.5489106 | 0.0719127 |
| GFP | Let7cAll | 0.6009550 | 0.6044708 | 0.51556223 | 0.5736627 | 0.0503471 |
| GFP | Let7f1All | 0.5269576 | 0.4880688 | 0.40747600 | 0.4741675 | 0.0609418 |
| GFP | Let7f2All | 0.7039111 | 0.5645864 | 0.60598900 | 0.6248288 | 0.0715475 |
| GFP | miR26a1All | 0.2354095 | 0.3187273 | 0.26144772 | 0.2718615 | 0.0426239 |
| GFP | miR26a1Base | 0.2110199 | 0.2456738 | 0.21815576 | 0.2249498 | 0.0182987 |
| GFP | miR26a2Base | 0.1459361 | 0.1679164 | 0.14448259 | 0.1527784 | 0.0131301 |
| GFP | miR26a2Stem | 0.1586252 | 0.1652927 | 0.15732646 | 0.1604148 | 0.0042740 |
| GFP | miR26bAll | 0.3597016 | 0.451126 | 0.38257302 | 0.3978002 | 0.0475763 |
| GFP | Let7f2WT | 1.0556041 | 0.9366958 | 0.90445501 | 0.9655849 | 0.0796081 |
| GFP | no amiRNA | 1 | 1 | 1 | 1 | 0 |
| GFP | Mock | 0.0003547 | 5.979E−05 | 4.62663 | 0.0001535 | 0.0001743 |

TABLE 3

| scaffold | replicate | Pten1523 Guide 10 kb | Pten1523 Passenger 10 kb | Total Sequences | | Pten1523 guide 10 kb/total reads*1e6 | Pten1523 passenger 10 kb/total reads*1e6 |
|---|---|---|---|---|---|---|---|
| Let7a1Loop | 1 | 283833 | 392 | 21214891 | | 13378.95 | 18.48 |
| Let7a1Loop | 2 | 651429 | 383 | 54625402 | Let7a1Loop | 11925.39 | 7.01 |
| Let7a2All | 1 | 132129 | 393 | 20007167 | | 6604.08 | 19.64 |
| Let7a2All | 2 | 76222 | 34 | 19618653 | Let7a2All | 3885.18 | 1.73 |
| Let7a3All | 1 | 335429 | 990 | 22841630 | | 14684.99 | 43.34 |
| Let7a3All | 2 | 860834 | 551 | 72130408 | Let7a3All | 11934.41 | 7.64 |
| Let7a3Loop | 1 | 173257 | 250 | 20263497 | | 8550.2 | 12.34 |
| Let7a3Loop | 2 | 294278 | 199 | 45484804 | Let7a3Loop | 6469.81 | 4.38 |
| Let7cAll | 1 | 285671 | 368 | 19939250 | | 14327.07 | 18.46 |
| Let7cAll | 2 | 392677 | 284 | 58874966 | Let7cAll | 6669.68 | 4.82 |
| Let7f1All | 1 | 249889 | 543 | 20048575 | | 12464.18 | 27.08 |
| Let7f1All | 2 | 468766 | 427 | 50402296 | Let7f1All | 9300.49 | 8.47 |
| Let7f2All | 1 | 318904 | 880 | 19896728 | | 16027.96 | 44.23 |
| Let7f2All | 2 | 171109 | 146 | 19759004 | Let7f2All | 8659.8 | 7.39 |
| Let7f2WT | 1 | 2321 | 19 | 19971469 | | 116.22 | 0.95 |
| Let7f2WT | 2 | 8473 | 105 | 53080657 | Let7f2WT | 159.63 | 1.98 |
| miR26a1All | 1 | 1120453 | 958 | 85715466 | | 13071.77 | 11.18 |
| miR26a1All | 2 | 1178757 | 592 | 65805213 | miR26a1All | 17912.82 | 9 |
| miR26a1Base | 1 | 382401 | 2009 | 31061405 | | 12311.13 | 64.68 |
| miR26a1Base | 2 | 990399 | 4655 | 54286572 | miR26a1Base | 18243.9 | 85.75 |
| miR26a2Base | 1 | 1381215 | 6716 | 105481002 | | 13094.44 | 63.67 |
| miR26a2Base | 2 | 629819 | 2785 | 24415887 | miR26a2Base | 25795.46 | 114.07 |
| miR26a2Stem | 1 | 922231 | 4517 | 40626154 | | 22700.43 | 111.18 |
| miR26a2Stem | 2 | 2203021 | 9151 | 67875045 | miR26a2Stem | 32457.01 | 134.82 |
| miR26bAll | 1 | 2489831 | 946 | 165376283 | | 15055.55 | 5.72 |
| miR26bAll | 2 | 301817 | 176 | 20178795 | miR26bAll | 14957.14 | 8.72 |
| miR155 | 1 | 816575 | 1313 | 82885883 | | 9851.8 | 15.84 |
| miR155 | 2 | 407397 | 1055 | 48993754 | miR155 | 8315.28 | 21.53 |
| miRE | 1 | 56860 | 46 | 21493302 | | 2645.48 | 2.14 |
| miRE | 2 | 48425 | 31 | 22359316 | miRE | 2165.76 | 1.39 |

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of generating amiRNAs and modifying a selected primary miRNA, comprising:

Applying a base modifying step to produce a single stranded region of at least 9 nucleotides and a GU dinucleotide in position −13 and −14, respectively from a Drosha cleavage site to form a base modified construct;

Applying a basal stem step to produce a double stranded RNA with a CHC motif and a bulge in position +8 from the Drosha cleavage site to form a base stem modified construct;

Applying a loop modifying step to substitute the endogenous loop region of the primary miRNA with the loop of a miRE, or another loop with same number of nucleotides and the GUG motif in the same position, to form a loop modified construct; and Operably linking the base modified construct, the basal stem modified construct, and the loop modified construct with the primary miRNA into an amiRNA construct.

2. The method of claim 1, wherein the total length of the modified basal stem is 9 to 13 base pairs with optimal length being 11 base pairs.

3. The method of claim 2, further comprising checking the base modified construct, the basal stem modified construct, and the loop modified construct to form an intended structure.

4. The method of claim 3, further comprising decreasing expression of PTEN mRNA by the amiRNA construct compared to miRE and miR155.

5. The method of claim 4, wherein the loop modified construct is loop region is at least 75% sequence identity to SEQ ID NOs: 3-9.

6. The method of claim 5, wherein the stem modified construct is at least 75% sequence identity to SEQ ID NO: 1.

7. The method of claim 4, wherein the loop region is at least 75% sequence identity to SEQ ID Nos: 10-11.

8. The method of claim 4, further comprising DROSHA and DICER processing of the amiRNA construct and detecting a guide strand at a magnitude of thousands more than the Passenger strand amount.

9. The method of claim 4, further comprising DROSHA processing and the amiRNA construct are processed more efficiently than miRE and miR155.

\* \* \* \* \*